United States Patent
Kiji et al.

(10) Patent No.: US 6,808,700 B2
(45) Date of Patent: Oct. 26, 2004

(54) DENTRIFICE COMPRISING CALCIUM CARBONATE GRANULES

(75) Inventors: Shinji Kiji, Tokyo (JP); Kazushi Oshino, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/096,660

(22) Filed: Mar. 14, 2002

(65) Prior Publication Data

US 2003/0031632 A1 Feb. 13, 2003

(30) Foreign Application Priority Data

Mar. 14, 2001 (JP) ........................................ 2001-072373

(51) Int. Cl.$^7$ .............................. A61K 7/16; C01F 5/24
(52) U.S. Cl. ...................... 424/49; 424/687; 423/220; 423/419.1; 423/430; 423/432
(58) Field of Search ........................ 424/49–58; 423/432

(56) References Cited

U.S. PATENT DOCUMENTS

| | | | | |
|---|---|---|---|---|
| 4,133,894 A | * | 1/1979 | Shibazaki et al. | 423/432 |
| 4,367,207 A | * | 1/1983 | Vanderheiden | 423/432 |
| 4,871,396 A | | 10/1989 | Tsujita et al. | |
| 5,019,148 A | * | 5/1991 | Moore | 71/11 |
| 5,149,521 A | | 9/1992 | Hirose et al. | |
| 5,205,493 A | * | 4/1993 | Adler et al. | 241/21 |
| 5,206,010 A | | 4/1993 | Inoue et al. | |
| 5,269,818 A | * | 12/1993 | Kunesh et al. | 423/432 |
| 5,275,651 A | * | 1/1994 | Minayoshi et al. | 423/432 |
| 5,296,002 A | * | 3/1994 | Passaretti | 423/432 |
| 5,376,343 A | * | 12/1994 | Fouche | 423/432 |
| 5,494,651 A | * | 2/1996 | Minayoshi et al. | 423/432 |
| 5,792,440 A | * | 8/1998 | Huege | 423/432 |
| 5,993,772 A | * | 11/1999 | Ninane et al. | 423/432 |
| 6,022,517 A | * | 2/2000 | Fairchild et al. | 423/432 |
| 6,156,286 A | * | 12/2000 | Fortier et al. | 423/432 |

FOREIGN PATENT DOCUMENTS

| | | |
|---|---|---|
| JP | 9-227348 | 9/1997 |
| JP | 10-36236 | 2/1998 |
| JP | 10-316547 | 12/1998 |
| JP | 2000-154126 A | 6/2000 |
| US | 20020172636 | * 11/2002 |
| WO | 200003949 | * 1/2000 |
| WO | 200192422 | * 10/2001 |

OTHER PUBLICATIONS

Patent Abstracts of Japan, Complete English Translation of JP2000–154126 Above (2000).
Patent Abstracts of Japan, Complete English Translation of JP 9–227348 Above (1999).
Patent Abstracts of Japan, Complete English Translation of JP 10–36236 Above (2000).
Patent Abstracts of Japan, Complete English Translation of JP10–316547 Above (2000).

* cited by examiner

Primary Examiner—Frederick F. Krass
(74) Attorney, Agent, or Firm—Oblon, Spivak, McClelland, Maier & Neustadt, P.C.

(57) ABSTRACT

A dentrifice comprising granules consisting essentially of calcium carbonate particles, the granules having an average size of 50 to 500 um and a crushing resistance of 1 to 20 g/granule, and the calcium carbonate particles having a primary particle size of 0.01 to 0.5 um.

16 Claims, No Drawings

DENTRIFICE COMPRISING CALCIUM CARBONATE GRANULES

BACKGROUND OF THE INVENTION

1. Field of the Invention

The present invention relates to a calcium-carbonate-granule-containing dentifrice which permits tactile sensation of cleaning effects in the mouth, can be prepared at a low cost, is free from adsorption of a flavoring component and is excellent in the refreshed feeling after use.

2. Description of the Related Art

Various oral compositions blended with granules or granule-like materials have conventionally been known. For example, medicinal components such as medicaments and enzymes are incorporated in granules to exhibit their effects or to give an aesthetic appreciation to the products. Some granules are adjusted to have a size or strength perceivable in the mouth. Described specifically, granules are prepared so that they can be perceived immediately after toothbrushing is started but can no more be perceived along the toothbrushing process, whereby the cleaning degree of plaque can be found by the tactile sensation. Some granules are, on the other hand, prepared so that they cannot be perceived at all from the very beginning of the toothbrushing, but the cleaning effect can be confirmed only with the eyes.

As an oral composition containing granules, a granule-containing dentifrice available by binding the granules with an inorganic or organic binder is proposed (Japanese Patent Application Laid-Open No. 299211/1989, Japanese Patent Application Laid-Open No. Hei 243815/1992). In addition, an oral composition substantially free of an organic and/or inorganic binder and comprising an aggregate formed of at least two fine-grain materials different in particle size is proposed (Japanese Patent Application Laid-Open 506885/1998).

Also proposed is use of a special synthesizing method for preparing particles substantially free of a binder and having a specific particle size and shape (Japanese Patent Application Laid-Open No. 59716/1998).

The above-described compositions or process, however, is accompanied with such a problem as cumbersome preparation processor high production cost, because it needs addition of an organic or organic binder, aggregation or granulation of a mixture of at least two different materials, or a special synthesizing process. Moreover, a flavoring gent contained in a dentifrice is adsorbed to the granules owing to the organic or inorganic binder or the special shape of the granules formed as a result of the synthesis, which disturbs the dentifrice from exhibiting refreshed feeling. Furthermore, when granulation is conducted without using particles other than ordinarily-employed polishing particles having an average primary particle size of 1 to 20 μm, it is difficult to control the particle size and crushing size.

An object of the present invention is therefore to provide a calcium-carbonate-granule-containing dentifrice which permits tactile sensation of cleaning effects in the mouth, can be prepared at a low cost, is free from al adsorption of a flavoring component and is excellent in the refreshed feeling after use.

Another object of the present invention is to provide a process for preparing the calcium carbonate granules and calcium carbonate granules prepared by the process.

SUMMARY OF THE INVENTION

Paying attention to the cohesive force of calcium carbonate particles having a markedly fine average primary particle size, the present inventors have found that incorporation of granules composed substantially singly of calcium carbonate in a dentifrice permits tactile sensation of the granules in the mouth and recognition of cleaning effects without giving almost no unpleasant feeling of foreign matters; enhances cleaning power without scratching tooth; and does not impair the refreshed feeling of the dentifrice.

In one aspect of the present invention, there is thus provided a dentifrice comprising granules which are composed substantially of calcium carbonates alone and which have an average granule size of 50 to 500 μm and the crushing resistance of 1 to 20 g/granule, said granules being obtained by binding thereto calcium carbonate particles having an average primary particle size of 0.01 to 0.5 μm.

In another aspect of the present invention, there is also provided a process for preparing calcium carbonate granules, which comprises granulating calcium carbonate particles of an average primary particle size of 0.01 to 0.5 μm, which has been obtained by allowing a $CO_2$ gas to pass through a calcium hydroxide suspension using a medium selected from a group consisting of calcium carbonate, calcium hydroxide and water, and then drying the resulting granules in a $CO_2$-containing gas.

In a further aspect of the present invention, there is also provided a process for preparing calcium carbonate particles, which comprises introducing, to a suspension containing 1 to 20 wt. % of calcium hydroxide, a $CO_2$-containing gas until a carbonating ratio reaches at least 90% but less than 100%, granulating the resulting suspension and then converting the resulting granules to calcium carbonate ones in a $CO_2$-containing gas.

In a still further aspect of the present invention, there is also provided the above-described process for preparing calcium carbonate granules, wherein the calcium carbonate granules thus obtained have an average granule size of 50 to 500 μm and crushing resistance of 1 to 20 g/granules.

The dentifrice according to the present invention permits tactile sensation of the granules in the mouth and recognition of their effects but hardly gives an unpleasant feel of foreign matters; has enhanced cleaning power without scratching tooth; and is excellent in refreshed feeling.

A process for preparing calcium carbonate granules is reduced in a production cost owing to the simplification of preparation steps and the granules obtained by this process are excellent as calcium carbonate granules for dentifrice.

BEST MODE FOR CARRYING OUT THE INVENTION

Calcium carbonate granules to be used in the present invention are obtained by granulating calcium carbonate particles having an average primary particle size of 0.01 to 0.5 μm, preferably 0.01 to 0.1 μm in order to impart the granules with a predetermined strength, thereby making it possible to sense the granules in the mouth and recognize their effects while hardly giving an unpleasant feel of foreign matters, and to enhance their cleaning power without scratching tooth. The average particle size of the calcium carbonate particles of the present invention means a value measured by microscopy (that is, a method of taking a photograph of particles magnified 40000 times through an electron microscope and visually measuring the particle size). The calcium carbonate granules are prepared by binding calcium carbonate particles while making use of their adhesiveness upon precipitation in water. This makes it possible to incorporate the granules in a dentifrice without impairing refreshed feeling. Calcium carbonate granules have an average granule size of 50 to 500 μm, preferably 75 to 250 μm. Such an average granule size makes it possible to sense the granules in the mouth and recognize their effects while hardly giving an unpleasant feel of foreign matters, and to enhance their cleaning power without scratching tooth. The average granule size of the granules means a value measured by the sifting method (sonic sifter, "SW-20-AT", manufactured by Tsutsui Rikagaku Kikai Co., Ltd.). The crushing resistance of the calcium carbonate granules is 1 to 20 g/granule, preferably 5 to 15 g/granule. Such crushing resistance makes it possible to sense the granules in the mouth and recognize their effects while hardly giving an unpleasant feel of foreign matters, and to enhance their cleaning power without scratching tooth. With regards to crushing resistance, crushing resistance of each of 10 to 20 granules having a granule size close to an average one is measured using a micro compression testing machine ("MCTM-500", manufactured by SHIMADZU CORP) and then, a mean value is calculated. Crushing resistance is expressed as this mean value. The calcium carbonate granules are desired to have similar resistance when incorporated in a toothpaste (wet state). They are preferred to have wet crushing resistance of 1 to 20 g/granule, preferably 5 to 15 g/granule. Such wet crushing resistance makes it possible to sense the granules in the mouth and recognize their effects while giving almost no unpleasant feel of foreign matters, and to enhance their cleaning power without scratching tooth.

Calcium carbonate granules can be prepared by allowing a $CO_2$ gas to pass through an aqueous suspension of calcium hydroxide to prepare calcium carbonate particles, granulating the particles and then, drying and sifting the resulting granules.

The above-described process is more preferred when calcium carbonate granules are prepared by granulating calcium carbonate particles of an average primary particle size of 0.01 to 0.5 μm, preferably 0.03 to 0.1 μm, which have been prepared by allowing a $CO_2$ gas to pass through an aqueous suspension of calcium hydroxide, by using one or more than one media selected from the group consisting of calcium oxide, calcium hydroxide and water; and then drying the resulting granules in a $CO_2$-containing gas. Drying in a high-temperature $CO_2$-containing gas is more preferred for controlling crushing resistance.

For controlling crushing resistance, preferred is addition of calcium oxide or calcium hydroxide serving as a medium in an amount of 0.05 to 10 parts by weight, preferably 0.1 to 1.0 part by weight based on 100 parts by weight of calcium carbonate particles.

Calcium carbonate particles having an average primary particle size of 0.01 to 0.5 μm can be prepared, for example, by reacting a calcium hydroxide suspension having a concentration of 1 to 20 wt. %, preferably 1 to 10 wt. %, at a reaction temperature of 5 to 35° C., preferably 5 to 20° C., a $CO_2$ concentration of 15 to 70 wt. %, preferably 30 to 50 wt. %, and a $CO_2$ gas flow rate of 500 to 1200 mL/min, preferably 500 to 1000 mL/min. The reaction time is 0.5 to 1.5 hours, preferably 0.5 to 1 hour.

The calcium carbonate granules to be used in the present invention can be prepared by granulating 100 parts by weight of the calcium carbonate particles prepared as described above while using 0 to 10 parts by weight of calcium oxide or calcium hydroxide and 10 to 70 parts by weight of water as media. For granulation, a suited method is selected as needed from roll granulation, extrusion granulation, compress granulation, agitating granulation, fluidized-bed granulation and spray drying granulation. The resulting granules thus formed are then dried for 1 to 5 hours in a gas stream containing 0 to 100 wt. % of a $CO_2$ gas, having a flow rate of 100 to 1000 mL/min and having a gas stream temperature of 80 to 200° C.

Most preferred is a process for preparing calcium carbonate granules by introducing a $CO_2$-containing gas into a suspension containing 1 to 20 wt. %, preferably 1 to 10 wt. % of calcium hydroxide until a carbonation ratio (a conversion ratio of calcium hydroxide in the suspension into calcium carbonate) reaches at least 90% but less than 100%; granulating the resulting suspension; and then converting the granules into calcium carbonate granules in a $CO_2$-containing gas.

In the dentifrice of the present invention, the calcium carbonate granules are preferably incorporated in an amount of 1 to 30 wt. %, preferably 2 to 20 wt. %, because such an amount permits tactile sensation of the granules in the mouth and recognition of their effects while giving almost no unpleasant feeling of foreign matters.

The dentifrice is prepared in a manner known per se in the art. It may contain another component ordinarily employed for dentifrices. As a thickening binder, carboxymethylcellulose sodium, hydroxyethyl cellulose, thickening silica, poly (sodium acrylate), carrageenan, xanthan gum, sodium alginate and the like are usable. As a medicinal component, allantoin, tranexamic acid, Vitamin E, Vitamin C, sodium monofluorophosphate, glycyrrhetinic acid, benzethonium chloride, cetylpyridinium chloride and the like are usable. As a flavoring agent, menthol, peppermint, spearmint, anethole, carvone, menthone, tymol, limonene, cineol, eugenol, cinnamic aldehyde, methyl salicylate, ethyl butyrate and the like are usable. In addition, a humectant, abrasive, sweetening agent, antiseptic, surfactant and the like can be added.

The granules prepared in such a manner are incorporated in various dentifrices such as toothpaste or tooth powder, but toothpaste is particularly preferred for aesthetic appreciation of granules.

EXAMPLES

Example 1

Preparation of Calcium Carbonate Granules (1) Calcium carbonate particles having an average primary particle size of 0.05 μm were granulated under stirring while using, based on 100 parts by weight of the particles, 0.1 part by weight of calcium hydroxide and 30 parts by weight of purified water as media, followed by hot air drying with a $CO_2$-containing gas in a drier of 200° C. Sifting through a sieve having an opening of 45 to 150 μm yielded granules having an average grain size of 95 μm and crushing resistance of 7.7 g/granule.

(2) A slurry of calcium carbonate particles having a slurry concentration of 30 wt. % and an average primary particle size of 0.02 μm was spray dried, whereby granules having an average granule size of 180 μm and crushing resistance of 5.5 g/granule were obtained.

(3) Calcium carbonate particles having an average primary particle size of 0.3 μm were granulated under stirring while using, based on 100 parts by weight of the particles, 0.5 part by weight of calcium hydroxide and 33 parts by weight of purified water as media, followed by hot air drying with a $CO_2$-containing gas in a drier of 200° C. Sifting through a sieve having an opening of 150 to 300 μm yielded granules having an average granule size of 220 μm and crushing resistance of 5.1 g/granule.

(4) Calcium carbonate particles having an average primary particle size of 0.04 μm were granulated under stirring while using, based on 100 parts by weight of the particles, 35 parts by weight of purified water as a medium, followed by hot air drying with a $CO_2$-containing gas in a drier of 200° C. Sifting through a sieve having an opening of 45 to 150 μm yielded granules having an average granule size of 110 μm and crushing resistance of 14.8 g/granule.

Preparation of Calcium Carbonate Granules (for Comparison)

Comparative Example 1

Calcium carbonate particles having an average primary particle size of 1 μm were granulated under stirring while using, based on 100 parts by weight of the particles, 30 parts by weight of purified water as a medium, followed by hot air drying with a $CO_2$-containing gas in a drier of 200° C. Sifting through a sieve having an opening of 45 to 150 μm yielded granules having an average granule size of 80 μm and crushing resistance of 4.5 g/granule.

Comparative Example 2

Calcium carbonate particles having an average primary particle size of 0.04 μm were granulated under stirring, while using, based on 100 parts by weight of the particles, 1.0 part by weight of calcium hydroxide and 30 parts by weight of purified water as media, followed by drying in a $CO_2$-containing gas. Sifting through a sieve having an opening of 45 to 150 μm yielded granules having an average granule size of 100 μm and crushing resistance of 24.5 g/granule.

Comparative Example 3

Calcium carbonate particles having an average primary particle size of 0.05 μm were granulated under stirring while using, based on 100 parts by weight of the particles, 0.1 part by weight of calcium hydroxide and 25 parts by weight of purified water as media, followed by drying in a $CO_2$-containing gas. Sifting through a sieve having an opening of 425 to 710 μm yielded granules having an average granule size of 560 μm and crushing resistance of 9.2 g/granule.

Comparative Example 4

Spray drying of a slurry of calcium carbonate particles having a slurry concentration of 30 wt. % and an average primary particle size of 0.02 μm yielded granules having an average granule size of 45 μm and crushing resistance of 5 g/granule.

Comparative Example 5

A slurry obtained by adding, to 44 wt. % of calcium carbonate particles having an average primary particle size of 1 μm, 33.6 wt. % of a silica sol as an inorganic binder and 22.4 wt. % of purified water was spray dried, whereby granules having an average granule size of 200 μm and crushing resistance of 8.2 g/granule.

Example 2

A dentifrice having the following composition was prepared.

| Component | Content | |
|---|---|---|
| Calcium carbonate granules (Table 1) | 15.0 | (wt. %) |
| Sodium monofluorophosphate | 0.68 | |
| Propylene glycol | 4.0 | |
| Sorbitol solution | 36.0 | |
| Carboxymethylcellulose sodium | 1.0 | |
| Silicic anhydride | 7.0 | |
| Sodium lauryl sulfate | 1.3 | |
| Saccharin sodium | 0.13 | |
| Paraoxybenzoic acid ester | 0.1 | |
| Flavoring agent | 1.0 | |
| Purified water | Balance | |
| Total | 100.0 | |

Properties other than average grain size and crushing resistance were measured in the below-described manner. The measuring results are shown in Table 1.

Measurement of Wet Crushing Resistance

A 50 wt. % slurry of granules was prepared using purified water. After the resulting slurry was allowed to stand at room temperature for 24 hours, the slurry was filtered to remove water and leave only the granules on a filter paper. Their wet crushing resistance was measured using a micro compression tester in a similar manner to that employed for crushing resistance.

Evaluation of Touch Feel of Granules and Feeling Upon Use of a Dentifrice

A panel of 10 experts used a dentifrice and evaluated touch feel of granules and refreshed feeling after use. The toothbrush used was a commercially available round-cut one. Perception degree, touch feel and refreshed feeling of granules in the oral cavity were evaluated in accordance with the below-described criteria.

Perception Degree

1. No granules were perceived.
2. Granules were perceived at the initial stage of toothbrushing, but perception dissipated during brushing.
3. Granules were perceived throughout toothbrushing.

Touch Feel

1. Good
2. Fair
3. Moderate
4. Slightly bad
5. Bad

Refreshed Feeling

1. Refreshed
2. Slightly refreshed
3. Neither refreshed nor unrefreshed
4. Not so refreshed
5. Not refreshed

TABLE 1

| Calcium carbonate granules | Invention products | | | | Comparative Products | | | | |
|---|---|---|---|---|---|---|---|---|---|
| | (1) | (2) | (3) | (4) | (Comp. Ex. 1) | (Comp. Ex. 2) | (Comp. Ex. 3) | (Comp. Ex. 4) | (Comp. Ex. 5) |
| Primary particle size ($\mu$m) | 0.05 | 0.02 | 0.3 | 0.04 | 1 | 0.04 | 0.05 | 0.02 | 2 |
| Granule size ($\mu$m) | 95 | 180 | 220 | 110 | 80 | 100 | 560 | 45 | 200 |
| Crushing resistance (g/granule) | 7.7 | 5.5 | 5.1 | 14.8 | 4.5 | 24.5 | 9.2 | 5.0 | 8.2 |
| Wet resistance (g/granule) | 7.0 | 5.3 | 4.8 | 14.6 | 0.1 | 24.7 | 9.0 | 4.8 | 8.2 |
| Perception of granules (number of experts) | | | | | | | | | |
| 1 | | | | | 10 | | | 8 | |
| 2 | 10 | 8 | 9 | 8 | | 3 | 5 | 2 | 9 |
| 3 | | 2 | 1 | 2 | | 7 | 5 | | 1 |
| Touch feel of granules (number of experts)*1 | | | | | | | | | |
| 1 | 1 | 5 | 5 | 2 | | | | | 5 |
| 2 | 6 | 4 | 5 | 6 | | | | | 5 |
| 3 | 3 | 1 | | 2 | | 2 | 2 | 2 | |
| 4 | | | | | | 5 | 3 | | |
| 5 | | | | | | 3 | 5 | | |
| Evaluation of refreshed feeling (number of experts) | | | | | | | | | |
| 1 | 5 | 6 | 6 | 5 | 4 | | | 5 | |
| 2 | 3 | 4 | 2 | 4 | 4 | 5 | 4 | 2 | 2 |
| 3 | 2 | | 2 | 1 | 2 | 3 | 5 | 3 | 5 |
| 4 | | | | | | 2 | 1 | | 3 |
| 5 | | | | | | | | | |
| Overall evaluation *2 | A | A | A | A | C | C | C | C | B |

*1: A question about touch feel of granules was not asked for those who did not perceive granules.
*2: Overall A: good, B: fair, C: bad With regards to the dentifrices (invention products) using calcium carbonate granules (1) to (4), granules were perceived at the initial stage of toothbrushing, were good in touch feel without giving an unpleasant feel of foreign matters and imparted the mouth with refreshed feeling.

What is claimed is:

1. A dentifrice comprising:
   a dentifrice vehicle; and
   granules consisting essentially of calcium carbonate particles, having an average granule size of 50 to 500 $\mu$m as measured by particle sifting, and a crushing resistance of 1 to 20 g/granule, wherein said calcium carbonate particles have an average primary particle size of 0.01 to 0.5 $\mu$m as measured by microscopy.

2. The dentifrice of claim 1, wherein the granules are obtained by granulating calcium carbonate particles having an average primary particle size of 0.01 to 0.5 $\mu$m or a slurry thereof in a medium selected from the group consisting of calcium oxide, calcium hydroxide and water and then drying the resulting granules in a $CO_2$-containing gas.

3. The dentifrice of claim 1, wherein the granules are obtained by introducing, to a slurry containing 1 to 20 wt. % of calcium hydroxide, a $CO_2$-containing gas until the carbonation ratio reaches at least 90% but less than 100%, granulating the resulting slurry and then carbonating the resulting granules in a $CO_2$-containing gas.

4. A process for preparing calcium carbonate granules consisting essentially of calcium carbonate particles, having an average granule size of 50 to 500 um, as measured by particle sifting, and a crushing resistance of 1 to 20 g/granule, which comprises granulating calcium carbonate particles obtained by passing a $CO_2$-containing gas through a medium of said particles and having an average primary particle size of 0.01 to 0.5 $\mu$m as measured by microscopy in, said medium being selected from the group consisting of calcium oxide, calcium hydroxide and water; and then drying the resulting granules in a $CO_2$-containing gas.

5. A process for preparing calcium carbonate granules consisting essentially of calcium carbonate particles, having an average granule size of 50 to 500 um, as measured by particle sifting, and a crushing resistance of 1 to 20 g/granule, and wherein said calcium carbonate particles have an average primary particle size of 0.01 to 0.5 um, as measured by microscopy, which comprises introducing, to a suspension containing 1 to 20 wt. % of calcium hydroxide, a $CO_2$-containing gas until the carbonation ratio reaches at least 90% but less than 100%, granulating the resulting suspension and then converting the resulting granules to calcium carbonate in a $CO_2$-containing gas.

6. A process for preparing calcium carbonate granules according to claim 4 or 5, wherein the calcium carbonate granules have an average granule size of 50 to 500 μm and crushing resistance of 5 to 15 g/granule.

7. The dentifrice of claim 1, wherein said calcium carbonate granules have an average granule size of 75 to 250 μm.

8. The dentifrice of claim 1, wherein said crushing resistance of said calcium carbonate granules is 5 to 15 g/granule.

9. The dentifrice of claim 1, wherein said calcium carbonate particles have an average primary particle size of 0.03 to 0.1 μm.

10. The dentifrice of claim 1, comprising 1 to 30 wt. % of said calcium carbonate granules.

11. The dentifrice of claim 1, comprising 2 to 20 wt. % of said calcium carbonate granules.

12. The dentifrice of claim 1, wherein said dentifrice further comprises a thickening binder.

13. The dentifrice of claim 1, wherein said dentifrice further comprises a medicinal component.

14. The dentifrice of claim 1, wherein said dentifrice further comprises a flavoring agent.

15. The dentifrice of claim 1, wherein said dentifrice further comprises an element selected from the group consisting of a humectant, an abrasive, a sweetening agent, an antiseptic, a surfactant and a mixture thereof.

16. A method of cleaning teeth comprising contacting with teeth, a dentifrice comprising:

a dentifrice vehicle; and granules consisting essentially of calcium carbonate particles having an average granule size of 50 to 500 μm as measured by particle sifting, and a crushing resistance of 1 to 20 g/granule, wherein said calcium carbonate particles have an average primary particle size of 0.01 to 0.5 μm as measured by microscopy.

\* \* \* \* \*